United States Patent [19]
Skelnik et al.

[11] Patent Number: 4,959,319
[45] Date of Patent: Sep. 25, 1990

[54] PROCESS OF CORNEAL ENHANCEMENT

[76] Inventors: Debra L. Skelnik, Box 344, Rte. 5, Cambridge, Minn. 55008; Richard L. Lindstrom, 1065 W. Ferndale Rd., Wayzata, Minn. 55391

[21] Appl. No.: 311,846

[22] Filed: Feb. 17, 1989

Related U.S. Application Data

[63] Continuation of Ser. No. 761,405, Aug. 1, 1985, abandoned.

[51] Int. Cl.$^5$ .......................... C12N 5/08; C12N 5/00; A01N 1/02
[52] U.S. Cl. .............................. 435/240.2; 435/240.21; 435/240.23; 435/240.241; 435/1
[58] Field of Search ..................... 435/1, 240.2, 241.21, 435/240.23, 240.241, 240.3, 240.31

[56] References Cited

U.S. PATENT DOCUMENTS 4,695,536  9/1987  Lindstrom et al. ...................... 435/1
4,696,917  9/1987  Lindstrom et al. ................... 514/54

OTHER PUBLICATIONS

Bashor, Methods in Enzymology, vol. 58, 119–137, 1979.
Freshney, Culture of Animal Cells, pp. 189–198, 1983.
Kaufman et al., American J. of Ophthalmology, pp. 112–114, Jul. 1984.
Sperling, Acta Ophthalmol., vol. 57, 269–276, 1979.
Gospodarowicz et al., Recent Progress in Hormone Research, vol. 35, 375–448, 1978.
Gospodarowicz et al., Exp. Eye Res. vol. 35, 259–270, 1982.
Mannagh et al. Arch Ophthal. vol. 74, 847–849, 1965.
Ham et al., Methods in Enzymology, vol. 58, 44–93, 1979.

Primary Examiner—Charles F. Warren
Assistant Examiner—Gail Poulos
Attorney, Agent, or Firm—Hugh D. Jaeger

[57] ABSTRACT

A process for establishing functional human corneal tissue consisting of an enhanced contact-inhibited endothelial monolayer derived from isolated human corneal endothelial cells with other integral corneal layers remaining intact. The process is divided into four integral parts.

1. Isolation of human corneal endothelial cells from donor corneas.

2. Establishment of a human corneal endothelial cell line which involves the establishment of primary cell cultures, proliferation, and continued maintenance and subculturing of these cells in vitro.

3. The utilization of long term storage of isolated human corneal endothelial cells at −80° C.

4. Utilizing these isolated corneal endothelial cells from the above processes to enhance the corneal endothelial monolayer of human donor corneas to be used for penetrating keratoplasty.

Two distinct methods of corneal endothelial enhancement may be utilized. In the first method, isolated human corneal endothelial cells are incorporated into the existing donor monolayer and re-establish a contact-inhibited functional monolayer, with a flattened, hexagonal configuration. In this procedure, the donor corneal endothelium remains intact and is supplemented with additional corneal endothelium. In the second method, isolated human corneal endothelial cells are seeded onto a denuded Descement's membrane and re-establish an intact cellular matrix, and form a contact-inhibited functional endothelial monolayer. In this procedure, the donor corneal endothelium is completely removed and replaced with new endothelial cells.

1 Claim, No Drawings

PROCESS OF CORNEAL ENHANCEMENT

CROSS REFERENCES TO CO-PENDING APPLICATIONS

This application is a continuation of application Ser. No. 06/761,405, filed Aug. 1, 1985, now abandoned.

BACKGROUND OF THE INVENTION

1. Field of the Invention

The field of the present invention is medical bio-engineering, and more particularly, pertains to ophthalmic applications in penetrating keratoplasty and cellular functions of human corneal endothelial cells.

2. Description of the Prior Art

Animal corneal endothelium such as rabbit, bovine, and feline, have been grown in cell culture using conventional techniques. The cultured cells closely resemble the parent, native endothelium. In culture, the endothelium synthesizes and deposits, in a polar fashion, a well organized basement membrane that contains molecules which are characteristic of all basement membranes. Cultured bovine corneal endothelial cells grown in tissue culture can be successfully transplanted back in vivo, resuming their normal pumping function. Feline corneal buttons coated with bovine corneal endothelial cells have been successfully transplanted in the same donor, resulting in functional endothelium. Limited success in higher primates has been demonstrated.

There is no cited evidence of human corneal primary or sub-cultured endothelium being successfully seeded onto either human or animal donors. Establishment of primary human corneal endothelial cell cultures were facilitated by outgrowth from isolated Descemet's membranes. This method of Descemet's dissection is technically difficult, with the additional disadvantage of introducing other contaminating cell types into the cell culture. Human endothelial cell growth from explants is often slow, as cells may take up to eight weeks to reach confluency. Enzymatic dissociation of human corneal endothelial cells from Descemet's membrane has resulted in the inability of these cells to reattach and form tight cell to cell junctions. Cellular attachment proteins were cleaved in the dissociation process unless extremely low levels of trypsin/EDTA were used. Establishment of primary human corneal endothelial cell cultures from donors over 20 years of age was limited or impossible. There is no cited evidence of primary cultures of either animal or human corneal cells being established from organ cultured tissue. Utilization of long term storage of human corneal endothelial cells at −80° C. has not been demonstrated.

The human cornea is a complex organ composed of three different tissues separated from each other by acellular layers which have the biochemical characteristics of basement membranes. These layers can be defined as the corneal epithelium, the acellular Bowman's membrane, the corneal stroma, the acellular Descemet's membrane, and the most important, the corneal endothelium. This endothelial monolayer maintains the clarity of the cornea by actively pumping salts and water out of the connective tissue stroma and into the anterior chamber of the eye. The corneal endothelium is a monolayer composed of highly contact-inhibited, flattened cells with a hexagonal configuration. The apical surface of the corneal endothelium is exposed to the aqueous humor, a nutritive body fluid that constantly bathes these cells.

The human corneal endothelium has a limited regenerative capacity, and the success of penetrating keratoplasty in humans depends on transplanting an adequate amount of functioning donor corneal endothelium and its maintenance and survival post-keratoplasty.

The present invention reconstructs from isolated corneal endothelial cells, maintained in vitro, the corresponding enhanced, functional corneal endothelial monolayer on human donor corneas. This procedure requires that corneal endothelium must be specifically isolated from the other layers of the donor cornea. These isolated endothelial cells must be maintained in vitro, proliferated actively; and upon reaching confluence, the cell must maintain both the morphological and functional capabilities of these cells in vitro.

SUMMARY OF THE INVENTION

The general purpose of the present invention pertains to isolation of human corneal endothelium from donor corneas. Post-Mortem time involved requires that donor human globes must be harvested within 24–48 of death. Primary cell cultures must be set up within this limited time period. Donor age is usually restricted to young donors. These prior art problems of establishing primary human corneal endothelial cell cultures within a limited time period, has been eliminated by the process of the present invention. Human corneas can be harvested up to 48 hours post-mortem and placed into organ culture for up to six months, and may still be utilized for establishing primary corneal endothelial cultures. Primary cultures can be established at any time during this organ culture time, without severe age restrictions. For optimum results the cornea should remain in organ culture for at least 5 days, to insure the sloughing of the epithelium.

In corneal endothelial cell isolation, direct enzymatic removal is used, replacing the technically difficult dissection of Descemet's membrane required for establishing primary human corneal endothelial cell cultures in previous methods. This method insures the removal of only corneal endothelial cells. Endothelial cells are the only cells exposed to the trypsin/EDTA solution. This trypsin/EDTA solution is buffered with additional HEPES buffer to insure the stability of the pH during endothelial cell isolation. Corneal epithelium cells are immersed in a trypsin inactivating media containing 15.6% fetal calf serum to provide protection to these cells during endothelial isolation. All sloughed epithelium has been removed from the culture medium. By direct microscopic observation, the integrity of Descemet's membrane can be established, and morphological changes of the endothelial cells after exposure to trypsin/EDTA solution can be closely monitored to decrease possible damage from this enzymatic solution. After the endothelial cells are flushed from Descemet's membrane, the remaining cornea can be examined microscopically to determine if all the endothelial cells have been removed. Experimental evidence indicates that the microtubules are not completely dissociated in this enzymatic process, and are rapidly reassembled after contact with the substratum. Media-1 containing chondroitin sulfate and fetal bovine serum has effectively protected the corneal endothelium from profound disruption of microtubules, usually associated with trypsinization. These two components of Media-1 have provided the necessary attachment factors and/or protected attachment proteins for isolated endothelial cells to attach, spread and proliferate on either isolated donor corneas or on tissue culture dishes.

In the culture media used in these procedures, 2-mercaptoethanol is used as a reducing thiol agent to replace the naturally occurring thiol reducing agents normally found in human aqueous. Human corneal endothelial cells are capable of using this reducing agent in both reduce and oxidized forms, similar to the way that these cells utilize glutathione. Glutathione is implicated in the possible functiOn Of reserving cysteine in a more stable and useable form. Cysteine may be the limiting amino acid for both protein synthesis and glutathione formation. When cysteine is added to the culture medium it is readily oxidized and unable for uptake into the cell. 2-mercaptoethanol is acting as a repeatable carrier for the cysteine into the cell, allowing for an increase of the cellular cysteine pool.

The use of Media-1 and Media-2 in the long term storage of human corneal endothelial cells has increased the recovery of viable cells after storage at −80° C. Chondroitinsulfate in addition to DMSO has increased the cryoprotectant properties of DMSO alone. This is the first time chondroitin sulfate has been used as a cryoprotectant. There are also no cited reports of successfully freezing human corneal endothelium at −80° C.

Although animal corneal endothelium has been successfully transplanted back in vitro, there is no cited evidence of similar seedings using human corneal cells. The process provides two methods of corneal enhancement. In the first method enzymatic dissociation of cell to cell junctions allows the cells to become separated from each other and expose areas of Descemet's membrane, but prevents the cells from becoming detached completely from the substratum. Newly seeded cells are then able to be incorporated into the existing monolayer, first attaching to the exposed areas of Descemet's and then forming new cell to cell contacts with the existing cells. The proteolytic actions of trypsin/EDTA are normally associated with wounding and wound healing, and allows the cells to be incorporated into the existing monolayer because cell to cell junctions must be re-formed. Chondroitin sulfate coats all the cells involved, and its negative charge helps in re-forming new cell to cell junctions, and new substratum attachments. In all the procedures using trypsin/EDTA, the solution is made up in a more defined culture media, Eagle's MEM, with additional HEPES buffering components added. These additions help to provide a more stable environment for enzymatic dissociation.

In the second corneal endothelial enhancement method the entire endothelial monolayer is enzymatically removed, and then the cornea is placed in Media-1. By placing the denuded cornea in this media, the surface of the cornea is coated not only with serum proteins, mainly fibronectin, but also with chondroitin sulfate which gives the corneal surface a negative charge that aids in the attachment of isolated corneal endothelial cells. Within 15 minutes the cells are attached, and begin to reform a contact-inhibited functional monolayer. The human corneal endothelial cells are capable of re-establishing a cell matrix that is similar to the native matrix.

Another general purpose of the present invention is establishment of human corneal endothelial cell line. After the isolation of human corneal endothelium from the donor cornea, the cells can be used for the establishment of primary corneal endothelial cultures and further subculturing of these cells. Human corneal cells that have been grown in cell culture may then be used for corneal enhancement or may be stored at −80° C. for future use. These isolated endothelial cells must be maintained in vitro, and proliferate actively; and upon reaching confluence they must maintain both the morphological and functional capabilities of these cells in vivo. Subcultured human corneal endothelium and subcultured human corneal endothelium that has been stored at −80° C. has been used successfully in human corneal enhancement procedures, with both the functional and morphological capabilities of these cells being maintained.

Human corneal endothelium have a limited regenerative capacity, and the success of penetrating keratoplasty in humans depends on transplanting an adequate amount of functioning donor corneal endothelium and its maintenance and survival post-keratoplasty. It is one object of the present invention to reconstruct from isolated endothelial cells, maintained in vitro, the corresponding enhanced, functional corneal endothelial monolayer on human donor corneas. This requires that corneal endothelium must be specifically isolated from the other layers of the donor cornea. These isolated endothelial cells must be maintained in vitro, and proliferate actively; and upon reaching confluence, must maintain both the morphological and functional capabilities of these cells in vivo.

In establishing a functional corneal tissue from isolated corneal endothelial cells, the process is in four integral parts.

1. Isolation of human corneal endothelial cells from donor corneas. This is a simplified process of endothelial cell removal. In the process of corneal endothelial cell isolation, direct enzymatic removal is used. This process insures the removal of only corneal endothelial cells. This trypsin/EDTA solution is buffered with additional HEPES buffer to insure the stability of the pH during endothelial cell isolation.
2. Establishment of a human corneal endothelial cell line. This involves the establishment of primary cell cultures, proliferation, continued maintenance and subculturing of these cells in vitro.
3. The utilization of long term storage of isolated human corneal endothelial cells at 80° C.
4. Use of these isolated corneal endothelial cells from the above processes enhances the corneal endothelial monolayer of donor corneas to be used for penetrating keratoplasty.
   A. Isolated human corneal endothelial cells are incorporated into the existing donor monolayer and re-establish a contact-inhibited functional monolayer with a flattened, hexagonal configuration. In this process the donor corneal endothelium remains intact and is supplemented with additional corneal endothelium.
   B. Isolated human corneal endothelial cells are seeded on to a denuded Descemet's membrane and re-establish an intact cellular matrix, and form a contact-inhibited functional endothelial monolayer. In this process the donor corneal endothelium is completely removed and replaced with new endothelial cells.

One significant aspect and feature of this process is the versatility of the isolated human corneal endothelium. Once isolated from fresh or organ cultured donor corneas, these human corneal endothelial cells may be used for: 1. Establishing primary cell cultures. 2. Long term storage at −80° C. 3. Corneal endothelial enhancement. Furthermore, human corneal cells that have been subcultured and/or frozen at −80° C. can be used for corneal enhancement. Isolated human corneal endothelial cells primary cultures, subcultured, and/or stored at −80° C. can be used for establishing a morphological and functional monolayer on synthetic corneal matrices or artificial corneas.

Another very significant aspect and feature of this enhancement and attachment process is that the process can be applied to other cell types.

Isolated vascular endothelial cells (umbilical cord and arota derived) primary cultures, subcultures and/or stored at −80° C. can be used for establishing a morphological and functional monolayer on intact or denuded vessels.

The process can also be applied to other specialized cells such as bone or cartilage cells, and used to enhance bone or cartilage tissue with limited modification of techniques.

Other specific cell types that can be utilized are adrenal medullar cells for cellular enhancement in diseased organs with Parkinson's syndrome. Another specific cell type is the pancreatic B-cell, which produces insulin, that could be utilized for cellular enhancement in diseased organs with type I diabetes.

DESCRIPTION OF THE PREFERRED EMBODIMENTS

Human Corneal Endothelial Enhancement

This procedure is of four integral parts:
1. Removal and isolation of human corneal endothelium from donor corneas.
2. Establishment by cell culture of human corneal endothelial cell line. This includes establishment of primary cell cultures, and continued maintenance and passage of these cells.
3. Utilizing a long term storage of isolated human corneal endothelial cells at −80° C.
4. Human corneal enhancement procedure:
   (a) intact human corneal monolayer; (b) denuded human corneal monolayer.

Standard Organ Culture Conditions for Human Corneas

Human donor globes are immersed in 1.0% povidone iodine in normal saline for three minutes, followed by a 1 minute immersion in normal saline. The globes are then rinsed with 12 cc of normal saline in a syringe fitted with a 18 gauge needle. Corneal scleral rims are removed and placed into organ culture at 34° C. in a humidified atmosphere (95% air:5% $CO_2$). Corneas are maintained in Mn-media comprised of modified Eagle's MEM with Earle salts and supplemented with 1.35% chondroitin sulfate (mixed isomers 99% pure, SIGMA), 2 mM L-glutamine, 25 mM HEPES, 90 ug/ml gentamycin sulfate and 10% fetal bovine serum 309 (Gibco). Corneas remained in organ culture until use, and the media is changed twice weekly.

Isolation of Human Corneal Endothelial Cells From Human Donor Corneas

Human corneas stored in standard organ culture conditions (Mn-Media) with 1.35% chondroitin sulfate and 10% fetal bovine serum (minimum time in culture 5 days) are removed from organ culture, and rinsed for 30 seconds in serumless media of Eagle's MEM with Earle salts, 2 mM L-glutamine, 25 mM HEPES, 90 ug/ml gentamycin sulfate. The cornea is placed in a petri dish, endothelial side up, and suspended on 0.1 ml of Media-1 to keep the epithelial surface moist during corneal endothelial cell isolation. Corneal endothelial cells are then trypsinized with a freshly prepared solution of 0.83% trypsin in a range 0.90–0.01% (DIFCO), 0.016 M EDTA in a range of 0.02–0.002 M EDTA, 33 mM HEPES in Eagle's MEM serumless media. This trypsin/EDTA solution is filtered through a 0.2 micron acrodisc filter. 0.05 ml to 0.1 ml of trypsin/EDTA solution is applied to the endothelial surface only. The amount of trypsin/EDTA solution applied is determined by the individual cornea. The trypsin/EDTA level should go up to the limbal edge only, to avoid possible removal of other unwanted cell types from the cornea.

After 15–40 minutes the trypsin/EDTA solution is removed, and rounded endothelial cells are gently flushed from Descemet s membrane with a 12 cc syringe fitted with a pasteur pipette plugged with cotton. Endothelial cells are isolated in 10 ml of Media-1 as now described and transferred into sterile, 15 ml polystyrene centrifuge tubes. The cell suspension is centrifuged at 1,100 RPM for 10 minutes and media is aspirated off, leaving a cell pellet which is resuspended in 0.1 to 1 ml of Media-1.

The cells are now ready for use in any of the established procedures of:
1. corneal endothelial enhancement (intact or denuded);
2. establishing primary cell cultures; or,
3. storage at −80° C.

Media Components for Media-1 and Media-2

Media-1:

Media-1 provides the components for the protection of the cell membrane and microtubular dissociation during isolation procedures, and allows initial cell attachment and cell spreading. The media is compounded of: Eagle's Minimum Essential Media with 25 mM HEPES buffer in a range of 10–25 mM, Earle's salts with 2 mM L-glutamine in a range of 1–3 mM, 1 mM sodium pyruvate in a range of 0.05–2 mM, 0.5 mM 2-mercaptoethanol in a range of 0.1–1 mM, 0.1 mM MEM non-essential amino acids in a range of 0.05–0.2 mM, 1.17% chondroitin sulfate (99% pure, mixed isomers, SIGMA) in a range of 0.1–10%, 80 ug/ml gentamycin sulfate in a range of 0–150 ug/ml, 3.9% Hank's Balanced Salt Solution without $CaCl_2$ and $MgSO_4 \cdot 7H_2O$ in a range of 0–15%, and 15.6% fetal bovine serum 309 (Gibco) in a range of 0–20%.

Media-2:

Media-2 provide components for cell proliferation, cell matrix formation and cell maintenance of functional corneal endothelial cell characteristics and is compounded of: Eagle's Minimum Essential Media with 25 mM HEPES buffer (range 10–25 mM), Earle's salts with 2 mM L-glutamine (range 1–3 mM), 1 mM sodium pyruvate (range 0.05–2 mM), 0.5 mM 2-mercaptoethanol (range 0.1–1 mM), 0.1 mm MEM non-essential amino acids (range 0.05–0.2 mM), 1.27% chondroitin sulfate (99% pure, mixed isomers, SIGMA) (range 0.1–10%), 80ug/ml gentamycin sulfate (0–150 ug/ml) and 4.23% Hank's Balanced Salt Solution without $CaCl_2$ and $MgSO_4 \cdot 7H_2O$ (range 0–15%), and 8.45% horse serum (range 0–20%).

Crude Retina Factor Preparation

Retinas are removed from human donor globes after decontamination procedures. The retina is separated from vitrous material and placed into 1 ml of serumless Media-2 in a 15 ml polystyrene centrifuge tube, and left at room temperature for 3 hours. The retina is then centrifuged for 10 minutes at 1,100 RPM's. The supernant is removed, sterile filtered with a 0.2 micron Acrodisc, and stored at $-80°$ C. until use. This crude preparation can be used to stimulate human corneal endothelial cell growth at 100 ug/ml (range 200 ng/ml–500 ug/ml). This retina factor-crude preparation can be substituted for either EDGF or FGF as described below when human corneal endothelial cells need stimulation.

Growth Factors

Additional components referred to as growth factors are to be added at specific times in specified procedures:
1. 0.1 mM ascorbic acid in a range of 0.01–0.2 mM
2. 10 ng/ml of FGF-Fibroblastic Growth Factor (Collaborative Research, Inc.) (range 1 ng/ml–10 ug/ml)
3. 300 ug/ml of ECGF-Endothelial Cell Growth Factor (SERAGEN, Inc.) (range 200 ng/ml 500 ug/ml)
4. 100 ng/ml of EGF-Epidermal Growth Factor (Collaborative Research, Inc.) (range 1 ng/ml–10 ug/ml)
5. 0.1 ng/ml Insulin in a range of 0.1 ng/ml–1 ug/ml
6. 100 ug/ml Crude Retina Factor (range 200 ng/ml to 500 ug/ml) (refer to crude retina factor preparation described in the above paragraph).
7. 10% Human umbilical cord serum (range 0.1–10%).
8. 0.3 mM Glutathione in a range 0.1 ug/ml to 0.5 mg/ml.
9. 0.01 ug/ml DL-$\alpha$-Tocopherol (Vitamin E) in a range 0.001 ug/ml to 1 ug/ml.
10. 0.11 mM Sialic acid in a range 0.001 mM to 1 mM.

Establishment of Human Corneal Endothelial Cell Line

After the cells are isolated from the human donor cornea in the above specified procedure, the cells are ready for use in the establishment of primary endothelial cell cultures. The cells are resuspended in 10 ml Media-1, and seeded onto treated flasks or wells. The cells are incubated for 24 hours in Media-1 until cells attach and then media is replaced with Media-2. The media is changed twice weekly, $\frac{2}{3}$ media is removed and replaced with fresh media where $\frac{1}{3}$ media is allowed to act as conditioned media. Cell cultures are maintained at 35.5° C. in a humidified atmosphere in 95% air:5% $CO_2$.

Establishing Cell Line

From an organ cultured cornea in standard Mn-media of 5 days at 34° C., cells are isolated from donor cornea in Media-1 (day 0) and seeded into treated flasks or wells. The cells are shifted to higher incubator temperature, 35.5° C., 95% air:5% $CO_2$.

The media is changed to Media-2 on day 1. The media is then changed twice weekly, $\frac{2}{3}$ media replaced with fresh media, $\frac{1}{3}$ acting as conditioned media.

Media-2 can be supplemented with ascorbic acid, and/or growth factors such as (FGF, ECGF, EPIDERMAL GROWTH factors or crude retina factor, human umbilical cord serum, glutathione, DL-$\alpha$-Tocopherol, Sialic acid.

At day 10–15 cells in flasks should be confluent and ready for subculture. Cells are usually best split at a 1:3 ratio when they are still actively undergoing mitosis.

Cells are ready for any of the established procedures: subculturing, corneal endothelial cell enhancement (intact or denuded, or for long term storage at $-80°$ C., as now described).

Subculturing Human Corneal Endothelium

The media is not totally removed from the culture flask, but enough media is left to cover the cells. This is also a protective agent for exposure to the trypsin-EDTA solution. The same concentration of trypsin/EDTA is used to subculture endothelial cells as used to isolate cells from donor corneas. 0.83% trypsin (range 0.9–0.01%), 0.016 M EDTA (range 0.02–0.002 M EDTA), 33 mM HEPES is made in serumless Eagle s MEM media. Trypsin/EDTA solution is filtered through a 0.2 micron acrodisk filter. 10 ml of trypsin/EDTA solution is applied to a 75 $cm^2$ flask, and the cells are watched constantly under an inverted microscope, while being gently agitated for 3–8 minutes. When cells are gently rounded up and start to release from the flask, 35–50 ml of Media-1 is added to stop the action of the trypsin. Six minutes of exposure to trypsin/EDTA solution is the standard time used for most cells. The cell suspension is then placed into 15 ml sterile, polystyrene centrifuge tubes and spun down for 10 minutes at 1,100 RPM. Additional Media-1 may be required to rinse down the flask to be sure of adequate cell removal. After centrifugation the media is aspirated off, where enough media should remain to cover the pelleted cells, the cells are resuspended in 0.1 ml–10 ml of Media-1. These cells are now ready for any of the established procedures.

Preparation of Treated Surfaces for Seeding of Cells

All flask (Corning) or wells (COSTAR) that are used are coated in the following procedure. 1% gelatin in normal saline is autoclaved for 15 minutes to sterilize, cool, and refrigerated until use. To coat one 75 $cm^2$ flask, 10 ml of 1% gelatin in normal saline is pipetted into the flask. The flask is rotated until the gelatin solution has covered the entire growing surface of the flask. The gelatin is allowed to sit at room temperature for 15–30 minutes. The gelatin solution is then aspirated off, and 5 ml of fetal bovine serum 309 (Gibco) is allowed to cover the entire growing surface of the dish for 10–30 minutes. The fetal bovine serum is aspirated off, and the flask is rinsed twice with 10 ml of Media-1.

Long Term Storage of Human Corneal Endothelial Cells at $-80°$ C.

Cells that are isolated from donor corneas or from cell cultures in the specified procedures are able to be frozen at $-80°$ C. After the cells are spun down into a cell pellet, the cells are resuspended in 1 ml of Media-1. This is mixed in 1:1 ratio with the following media:

| 30 ml of Media-2 | | Media 1 |
|---|---|---|
| 50 ml of horse serum | 1 ml:1 ml | with |
| 20 ml of DSMO | | suspended |
| (Dimethylsulfoxide) | | cells | total volume per cryotube 2 ml

Combine freezing mixture with suspended cells quickly, place in cryotube (2 ml per tube), and put immediately into −80° C. freezer. To thaw out the cells, remove from freezer and place directly in a 35° C. water bath until thawed out 1 minute). Put each 1 ml into 9 ml of Media-1 and resuspend cells thoroughly, and centrifuge for 10 minutes at 1,100 RPM. Aspirate off media and resuspend pellet in 10 ml of Media-1, repeat centrifugation. Resuspend the cell pellet in 10 ml of media (or appropriate amount), and cells are ready for any of the specified procedures.

Human Corneal Endothelial Enhancement Procedure

Conditions have been defined to utilize primary and subcultured human corneal endothelial cells in vitro to enhance human corneal endothelial cells by 1.73 times the original count. This seeding technique allows human corneal endothelial cells to be incorporated into the existing monolayer, and re-establish a contact inhibited hexagonal configuration, confirmed by scanning electron microscopy and alizarin red staining.

Preparation of the Recipient Human Cornea Intact Monolayer for Putting Cells into Existing Monolayer Organ cultured corneas stored under standard conditions in Mn-media containing both 1.35% chondroitin sulfate and 10% fetal bovine serum 309 (Gibco), can be used successfully for this procedure. The preferred media for corneal storage is Media-2. Flexibility of medias allows a greater choice in the determination of corneal use.

The cornea is removed from organ culture and rinsed for 30 seconds in serumless media-2. The cornea is placed in a petri dish, endothelial side up, suspended on 0.1 ml of Media-1, to keep the epithelial surface moist during corneal endothelial enhancement. The endothelial monolayer is exposed to a freshly prepared solution of 0.83% trypsin (DIFCO) (range 0.9%–0.01%), 0.016 M EDTA (range 0.02–0.002 M EDTA), 33 mM HEPES made up in Hank's balanced salt solution without $CaCl_2$ and $MgCl_2\text{-}7H_2O$. The trypsin/EDTA solution is filtered through a 0.2 micron acrodisk filter. 0.5 ml to 0.1 ml of trypsin/EDTA solution is applied to the endothelial surface only. Trypsin/EDTA solution may be reapplied 1 to 3 times, during the incubation time of 5 to 30 minutes, depending on the condition of the endothelial cells involved. Human corneas vary greatly in the time needed to break the cell to cell bonds of the existing endothelial monolayer. The average time involved is usually 12 minutes, with 2 changes of the trypsin/EDTA solution. It is crucial that the corneal endothelium is observed constantly under the microscope to determine the length of time needed for the breakage of cell to cell bonds. The corneal endothelial cells must have become separated from each other and expose Descemet's membrane for the procedure to work successfully. After the corneal endothelium has exhibited the necessary morphologic changes, the trypsin/EDTA solution is removed, the cornea is placed in 15 ml of Media-1 in a petri dish and incubated at 35.5° C. for 5–10 minutes in a humidified atmosphere with 95% air:5% $CO_2$. Corneal endothelial cells isolated from donor corneas, primary or passed cultures or from storage at −80° C., can be used to enhance the prepared corneal endothelial monolayer.

Human corneal endothelial cells that were prepared in the prescribed manner are suspended in 0.1–0.2 ml of Media-1 after final pelleting of isolated cells. All pipettes that are used for this procedure are cotton plugged and rinsed in distilled water to remove any dust or particles that may interfere with procedure. The isolated cells are evenly suspended in the pasteur pipette. The recipient cornea is removed from the incubator and placed in a new petri dish filled with Media-1 only up to the scleral rim of the cornea. The endothelial side of the cornea does not come in contact with the media. The cell suspension is then pipetted directly onto the endothelium 3 to 5 drops). The cornea is then placed back into the incubator for 10 minutes at 35.5° C. in a humidified atmosphere with 95% air:5% $CO_2$. The number of cells seeded onto the cornea is determined by the existing endothelial cell count of the recipient. After 30–60 minutes the cells have settled onto the existing monolayer and are attached. At this time, it is possible to add additional Media-1 without disturbing attached cells. After 24 hours the cornea is gently rinsed to remove any non-adherent cells, and the media is changed to Media-2 with 150 ug/ml to 300 ug/ml of ECGF and/or 10 ng/ml of FGF. The cornea is ready to be transplanted at 9 days post seeding. The media should be changed every 3 to 4 days.

Preparation of the Recipient Human Cornea Denuded Corneal Endothelium

Organ cultured corneas stored under standard conditions in media containing both 1.35% chondroitin sulfate and 10% fetal bovine serum 309, can be used successfully for this procedure. The preferred media for corneal storage is Media-2. Flexibility of medias allows a greater choice in the determination of corneal use. The cornea is removed from organ culture and rinsed for 30 seconds in serumless Media-2. The cornea is placed in a petri dish, endothelial side up, and suspended on 0.1 ml of Media-1, to keep the epithelial surface moist during corneal endothelial enhancement. The endothelial monolayer is exposed to a freshly prepared solution of 0.83% trypsin (DIFCO) (range 0.90%–1%), 0.016 M EDTA (range 0.2 M–0.002 M EDTA), 0.33 mM HEPES made up in serumless Eagle's MEM. The trypsin/EDTA solution is filtered through a 0.2 micron acrodisc filter. 0.05 to 0.1 ml of trypsin/EDTA solution is applied to the endothelial surface only. Trypsin/EDTA solution may be reapplied 1 to 3 times, during the 15–40 minute incubation depending on the condition of the endothelial cells involved. In this case, the corneal endothelium will be totally removed enzymatically from Descemet's membrane. It is crucial that the corneal endothelium is observed constantly under the microscope to determine the length of time needed for the cells to become detached from their matrix, but not long enough to damage the existing matrix or underlying stromal cells. After 15–40 minutes, the trypsin/EDTA solution is removed, and rounded endothelial cells are gently flushed from Descemet's membrane with 12 cc syringe fitted with a pasteur pipette plugged with cotton. The cornea is then placed in 15 ml of Media-1 in a petri dish and incubated at 35.5° C. for 10–20 minutes in humidified atmosphere with 95% air:5% $CO_2$. Corneal endothelial cells isolated from donor corneas, primary or passed cultures or from storage at −80° C., can be used to seed this denuded Descemet's membrane. Human corneal endothelial cells that were prepared in the prescribed manner are suspended in 0.1–0.2 ml of Media-1 after final pelleting of isolated cells. All pipettes that are used for this procedure are cotton plugged and rinsed in distilled water to remove any dust or particles that may interfere with procedure. The isolated cells are evenly suspended in the pasteur pipette. The recipient cornea is removed from the incubator and placed in a new petri dish filled with Media-1 only up to the scleral rim of the cornea. The denuded endothelial side of the cornea does not come in contact with the media. The cell suspension is then pipetted directly onto the denuded Descemet's membrane (3 to 5 drops). The cornea is then placed back into the incubator at 35.5° C. in a humidified atmosphere with 95% air:5% $CO_2$. The number of cells seeded onto the cornea is determined by the density desired in the final seeded corneal endothelium. After 30-60 minutes the cells have settled onto the existing monolayer and are attached. At this time, it is possible to add additional Media-1 without disturbing attached cells. After 24 hours the cornea is gently rinsed to remove any nonadherent cells, and the media is changed to Media-2 with 150 ug/ml to 300 ug/ml of ECGF and/or 10 ng/ml of FGF. The cornea is ready to be transplanted at 9 days post seeding. The media should be changed every 3 to 4 days.

We claim:

1. A process for enhancing an intact endothelial monolayer of a human donor cornea to be used in penetrating keratoplasty, the method comprising:
   a. enzymatically isolating corneal endothelial cells from a human donor cornea;
   b. optionally, one of:
      1. in a suitable medium, establishing a primary line of cells isolated in (a), proliferating them and then maintaining them, or,
      2. storing the cells isolated in (a) at a temperature of about −80° C.; and then,
   c. seeding an enzymatically treated intact endothelial monolayer of a donor cornea with the cells prepared in (a) or (b)(1) or the thawed cells of (b)(2).

* * * * *